US011000465B2

(12) United States Patent
Hodgkinson

(10) Patent No.: US 11,000,465 B2
(45) Date of Patent: *May 11, 2021

(54) COMPOSITION

(71) Applicant: BLOCK DRUG COMPANY INC, Ewing, NJ (US)

(72) Inventor: John Hodgkinson, Surrey (GB)

(73) Assignee: Block Drug Company, Inc., Ewing, NJ (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/718,943

(22) Filed: Dec. 18, 2019

(65) Prior Publication Data

US 2020/0188264 A1    Jun. 18, 2020

Related U.S. Application Data

(60) Division of application No. 15/822,731, filed on Nov. 27, 2017, now Pat. No. 10,548,827, which is a continuation of application No. 14/237,421, filed as application No. PCT/EP2012/065378 on Aug. 7, 2012, now abandoned.

(30) Foreign Application Priority Data

Aug. 9, 2011 (GB) ..................... 1113754

(51) Int. Cl.
| | | |
|---|---|---|
| *A61K 8/46* | (2006.01) | |
| *A61Q 11/00* | (2006.01) | |
| *A61K 8/44* | (2006.01) | |
| *A61K 8/40* | (2006.01) | |

(52) U.S. Cl.
CPC ................ *A61K 8/463* (2013.01); *A61K 8/40* (2013.01); *A61K 8/442* (2013.01); *A61K 8/466* (2013.01); *A61Q 11/00* (2013.01); *A61K 2800/31* (2013.01); *A61K 2800/596* (2013.01)

(58) Field of Classification Search
CPC .......... A61K 8/463; A61K 8/40; A61K 8/466; A61K 8/442; A61K 2800/596; A61K 2800/31; A61Q 11/00
See application file for complete search history.

(56) References Cited

U.S. PATENT DOCUMENTS

| | | | |
|---|---|---|---|
| 3,574,824 A | 4/1971 | Echeandia et al. | |
| 4,060,599 A | 11/1977 | Cordon | |
| 4,647,451 A | 3/1987 | Piechota, Jr. | |
| 5,670,137 A | 9/1997 | Ascione | |
| 5,882,630 A | 3/1999 | Gates et al. | |
| 6,696,045 B2 | 2/2004 | Yue et al. | |
| 2004/0223921 A1 | 11/2004 | Rau et al. | |

FOREIGN PATENT DOCUMENTS

| | | |
|---|---|---|
| KR | 20110026697 | 3/2011 |
| WO | WO 96/03108 | 2/1996 |
| WO | WO 2002/038119 | 5/2002 |
| WO | WO 2005/063185 | 7/2005 |
| WO | WO 2008/145475 | 12/2008 |
| WO | WO2010/045344 | 4/2010 |
| WO | WO 2010/115037 | 10/2010 |
| WO | WO 2011/088199 | 7/2011 |

OTHER PUBLICATIONS

Database WPI Week 201131, Thomson Scientific, London, GB; AN 2011-C88420; XP002719038, & KR 2011 0026697 A (Amorepacific Corp); Mar. 16, 2011 abstract.

*Primary Examiner* — Lezah Roberts
(74) *Attorney, Agent, or Firm* — Roshni A. Sitapara

(57) ABSTRACT

The invention relates to non-aqueous dentifrice compositions comprising a surfactant system. The surfactant system consists of a combination of surfactants i.e. a betaine and a taurate surfactant; or a betaine and an alkyl sulphate surfactant; or a betaine, a taurate and an alkyl sulphate surfactant.

5 Claims, No Drawings

COMPOSITION

FIELD OF THE INVENTION

The present invention relates to a composition in particular to a non-aqueous dentifrice composition comprising a novel surfactant system. In particular the invention relates to a non-aqueous dentifrice composition comprising a combination of surfactants i.e. a betaine and a taurate surfactant; or a betaine and an alkyl sulphate surfactant; or a betaine, a taurate and an alkyl sulphate surfactant. Such a dentifrice composition demonstrates pleasant organolpetic properties and is of use in oral care.

BACKGROUND OF THE INVENTION

There are many dentifrice additives which are incompatible with aqueous systems of typical dentifrice formulations. One way of overcoming this incompatibility problem is to formulate such additives in a non-aqueous (anhydrous) formulation. However in addition to circumventing the water incompatibility problem, such formulations must also be successful from a consumer acceptance standpoint and demonstrate, for example, acceptable taste, consistency and adequate foaming on brushing of teeth.

U.S. Pat. No. 3,574,824 (Warner-Lambert) describes an anhydrous toothpaste base comprising inter alia an oil, a combination of polyethylene glycols and a non-toxic, non-ionic emulsifier which is a mixture of glycerides. U.S. Pat. No. 3,574,824 discloses that an experimental paste was made using oily liquids, such as vegetable oil or extra light mineral oil, and a suitable surfactant. However when the paste was brought into contact with water during brushing there was insufficient foaming in the oral cavity. This was thought to be due to the fact that the foaming agent (sodium lauryl sulphate) was "hindered" in the anhydrous mass and was unable to concentrate at the air-water interface during brushing to form air bubbles or foam.

U.S. Pat. No. 4,647,451 (Colgate-Palmolive Company) describes anhydrous dentifrice compositions having desirable rheological, sensory and hygienic characteristics containing a polysaccharide gum and glycerine humectant. According to U.S. Pat. No. 4,647,451, such compositions comprise organic surface active agents which may be anionic, non-ionic, ampholytic, or cationic in nature. Compositions exemplified therein contain sodium lauryl sulphate as the sole surfactant.

U.S. Pat. No. 5,670,137 (L'Oreal) describes a dentifrice composition containing an anhydrous medium comprising glycerine, at least one hydroxyethylcellulose, at least one pyrogenetic silica. According to U.S. Pat. No. 5,670,137 such a composition also contains one or more foaming surfactants which may be anionic, amphoteric, zwitterionic, cationic or non-ionic. Compositions exemplified therein contain sodium lauryl sulphate as the sole surfactant.

WO96/03108 (SmithKline Beecham plc) and WO 2002/038119 (SmithKline Beecham plc) both describe non-aqueous dentifrice compositions. Anionic, cationic, non-ionic and amphoteric surfactants are disclosed for use as suitable surfactants. A particularly preferred anionic surfactant is identified as sodium methyl cocyl taurate, marketed under the name "Adinol CT 95", this being the sole surfactant exemplified for use in the compositions therein.

WO2005/063185 (Novamin Technology Inc.) describes non-aqueous compositions of bioactive glass particulates in a non-aqueous carrier of the type disclosed in U.S. Pat. No. 5,882,630 (Gates). U.S. Pat. No. 5,882,630 corresponds to the US patent derived from WO96/03108, discussed above. According to WO2005/063185, compositions therein may optionally comprise agents conventionally used in dentifrice formulations including, for example, a foaming agent such as sodium lauryl sulphate. Compositions exemplified therein contain sodium lauryl sulphate as the sole surfactant.

WO2010/115037 (Colgate-Palmolive Company) describes non-aqueous compositions comprising carrageenan or a carboxymethylcellulose gum, a humectant and a bioacceptable and bioactive glass. According to WO2010/1155037, compositions therein may comprise additives conventionally used in dentifrice compositions including for example a surfactant such as sodium lauryl sulphate. Compositions exemplified therein contain sodium lauryl sulphate as the sole surfactant.

Whilst the non-aqueous compositions described in the prior art address some of the problems encountered with formulating dentifrice additives that are incompatible with aqueous-based systems, there nevertheless remains a need for alternatives. Ideally such alternative compositions should further demonstrate one or more properties that are key drivers of consumer acceptance including, for example, having consumer-acceptable organolpetic properties. Ideally the organolepic properties of such a composition will be at least as good as or preferably improved over those seen in comparable, marketed non-aqueous dentifrice products.

It is an object of the invention to provide such a composition.

SUMMARY OF THE INVENTION

In one aspect the invention provides a non-aqueous dentifrice composition comprising a carrier wherein the carrier consists of a surfactant system consisting of a first surfactant which is a betaine in combination with a second surfactant which is a taurate or an alkyl sulphate or mixtures thereof.

Surprisingly it has been discovered that a non-aqueous composition comprising a surfactant system consisting of a combination of surfactants, specifically a betaine and a taurate, or a betaine and an $C_{10\text{-}20}$ alkyl sulphate, provides significantly superior organoleptic properties compared to that observed for a composition comprising a single, sole surfactant (sodium lauryl sulphate). Such superior organoleptic properties include one or more of improved mouthfeel, improved foam dispersion and consistency, and improved foam characteristics such as intensity and density, all of which are desired attributes in a dentifrice composition. In some embodiments foam characteristics are improved without modifying significantly on taste properties.

DETAILED DESCRIPTION OF THE INVENTION

As used herein, the term "non-aqueous" means anhydrous or substantially free of water. The individual components of the non-aqueous composition may contain limited amounts of water as long as the overall composition remains substantially free of water.

As used herein the term "dentifrice" includes any semi-solid preparation in the form of a paste, cream or gel for use in cleaning all or a portion of the oral cavity of an individual.

As used herein the term "oral cavity" means an individual's teeth and gums including all periodontal regions including teeth down to the gingival margins and/or the periodontal pockets.

A composition according to the invention comprises a surfactant system. The surfactant system consists of a first surfactant and a second surfactant. In certain embodiments the surfactant system consists of a first surfactant and a second surfactant wherein the second surfactant consists of a mixture of surfactants.

A first surfactant for use in the surfactant system of a composition according to the invention belongs to the class of compounds known as betaines. Structurally, betaine compounds contain an anionic functional group such as a carboxylate functional group and a cationic functional group such as quaternary nitrogen functional group separated by a methylene moiety. They include n-alkyl betaines such as cetyl betaine and behenyl betaine, and n-alkylamido betaines such as cocoamidopropyl betaine. In one embodiment the betaine is cocoamidopropyl betaine, commercially available under the trade name Tego Betain. Suitably the betaine is present in an amount ranging from about 0.05 to about 4% by weight of the non-aqueous composition, for example from about 0.2 to about 2.0% by weight of the non-aqueous composition.

A second surfactant for use in the surfactant system of a composition according to the invention is selected from a taurate or a $C_{10-20}$ alkyl sulphate surfactant. Taurate surfactants useful in the present invention are salts of fatty acid amides of N-methyl taurine. They conform generally to the structural formula:

$$RC(O)N(CH_3)CH_2CH_2SO_3M$$

Where RC(O)— represents a fatty acid radical and M represents sodium, potassium, ammonium or triethanolamine. Fatty acids having carbon chain lengths of from 10 to 20, including those derived from coconut, palm and tall oil are used. In one embodiment the fatty acid is derived from coconut. In one embodiment, sodium salts are used. In one embodiment the taurate is sodium methyl cocyl taurate. This taurate surfactant is sold under the trademark by Adinol CT by Croda.

The taurate surfactant may be present in an amount from about 0.1 to about 10% of the non-aqueous composition. In one embodiment the taurate surfactant is present in an amount from about 0.1 to about 5% by weight of the non aqueous composition. In one embodiment the taurate surfactant is present in an amount from about 0.5 to about 2.0% by weight of the non-aqueous composition.

Alkyl sulphate surfactants of use in the invention have the following structural formula:

$$R^1OSO_3M$$

$R^1$ represents a fatty alcohol moiety and M represents sodium, potassium, ammonium or triethanolamine. Fatty alcohols having carbon chain lengths of from about 10 to about 20, including those derived from coconut, palm oil and tall oil. In one embodiment, the fatty alcohol is lauryl alcohol. In one embodiment, a sodium salt is used. In one embodiment the alkyl sulphate is sodium lauryl sulphate.

The alkyl sulphate surfactant may be present in an amount from about 0.1 to about 10% of the non-aqueous composition. In one embodiment the alkyl sulphate surfactant may be present in an amount from about 0.1 to about 5% by weight of the non aqueous composition. In one embodiment the alkyl sulphate surfactant is present in an amount from about 0.5 to about 2.0% by weight of the non-aqueous composition.

In certain embodiments, the surfactant system consists of a first surfactant which is a betaine, and a second surfactant which consists of a mixture of a taurate and a $C_{10-20}$ alkyl sulphate surfactant as hereinabove described. In one embodiment the surfactant system consists of a first surfactant which is a betaine and second surfactant which consists of a mixture of sodium methyl cocyl taurate and sodium lauryl sulphate.

In one aspect a composition according to the invention comprises a dentifrice additive that is unstable or incompatible with an aqueous environment.

An example of such an additive is a bioactive glass of the type disclosed in WO96/10985, WO 97/27158 and WO 99/13852. In an aqueous environment such a bioactive glass releases ions causing a significant increase in pH which can adversely affect the stability (especially upon long-term storage) of any excipients contained within the dentifrice. Formulating a bioactive silica-based glass in the non-aqueous dentifrice of the present invention prevents the release of ions within the dentifrice thereby controlling pH and increasing long-term storage stability of the dentifrice.

In one embodiment the bioactive glass for use in the invention has a composition consisting of about 45% by weight silicon dioxide, about 24.5% by weight sodium oxide, about 6% by weight phosphorus oxide, and about 24.5% by weight calcium oxide. One such bioactive glass is available commercially under the trade name, NovaMin®, also known as 45S5 Bioglass®.

The bioactive glass is present in an amount ranging from about 1 to about 20% by weight of the non-aqueous composition. In one embodiment, the bioactive glass is present in an amount from about 1 to about 15% by weight of the non-aqueous composition. In an alternative embodiment, the bioactive glass in the non-aqueous composition is present in an amount from about 1 to about 10% by weight of the non-aqueous composition. In a further alternative embodiment the bioactive glass is present in an amount from about 2 to about 8% by weight of the non-aqueous composition.

In one embodiment of the invention, a dentifrice composition is prepared comprising the following components in percent by weight:

| | |
|---|---|
| Bioactive glass | about 1 to about 10 |
| Betaine | about 0.05 to about 4 |
| Taurate | about 0.5 to about 2 |
| Carbomer | about 0.3 to about 1 |
| Glycerin | about 50 to about 70 |
| Polyethylene glycol | about 15 to about 25 |

In one embodiment of the invention, a dentifrice composition is prepared comprising the following components in percent by weight:

| | |
|---|---|
| Bioactive glass | about 1 to about 10 |
| Betaine | about 0.05 to about 4 |
| SLS | about 0.5 to about 2 |
| Carbomer | about 0.3 to about 1 |
| Glycerin | about 50 to about 70 |
| Polyethylene glycol | about 15 to about 25 |

The carrier comprising the surfactant system is a non-aqueous carrier and is substantially non-reactive with bioactive glass particulates (or other dentifrice additives that are unstable or incompatible with an aqueous environment) and is suitable for use in a dentifrice composition. Suitable non-aqueous carrier formulations are described, for example, in U.S. Pat. No. 5,882,630, issued to Gates et al. (1999).

A non-aqueous carrier useful in the present invention typically comprises a thickening agent and one or more formulation solvent(s). Optionally, a dentally acceptable abrasive may be included in the non-aqueous carrier.

Advantageously, a thickening agent is present in the formulation to give the product a rheology closer to that of a conventional dentifrice. Suitably the thickening agent comprises a carboxyvinyl polymer such as a carbomer. A carbomer comprises synthetic high molecular-weight cross-linked polymers of acrylic acid. The polymer chains formed of repeating units of acrylic acid may be cross-linked with, for example: allyl sucrose to provide a carbomer available commercially in one form as Carbopol™ 934; ethers of pentaerythritol to provide a carbomer available commercially in one form as Carbopol™ 974; or with divinyl glycol, available commercially in one form as Noveon™ AA-1. Carbopol™ polymers are manufactured by B.F. Goodrich Company. In one embodiment the carboxyvinyl polymer comprises Carbopol™ 974. The carboxyvinyl polymer may be present in the range of from about 0.1 to about 7.5% by weight of the non-aqueous composition. In one embodiment the carboxyvinyl polymer is present in an amount from about 0.3 to about 1.0% by weight of the composition.

Suitably a composition according to the invention may further comprise an inorganic thickening agent such as a thickening silica. Suitably, the thickening agent is a thickening silica, for example, a colloidal hydrated silica, available commercially for example as Sident 22S or Syloid 244FP.

In one embodiment the thickening silica is present in the range of from about 0 to about 15%, suitably from about 5.0 to about 15.0% by weight of the non-aqueous composition.

Suitable solvents for use in the present invention include glycerin, sorbitol, propylene glycol, polyethylene glycol or mixtures thereof. In one embodiment the solvent comprises glycerin. It is well known that commercially available glycerin may contain between 0.1-2.0% by weight of water which is in association with the glycerin. Typically this amount is <0.5% for example between 0.1-0.5% by weight of the glycerin. This small amount of water is bound to the glycerin and is therefore not available to the other ingredients. The skilled person would still consider a composition containing glycerin as being non-aqueous. The solvent should in any case be as anhydrous as possible.

In one embodiment the solvent comprises polyethylene glycol. Suitably, the polyethylene glycol will be selected from PEG 300, PEG 400 and mixtures thereof. In one embodiment the polyethylene glycol comprises PEG 400.

In one embodiment the solvent comprises a mixture of glycerin and polyethylene glycol.

The formulation solvent is used to make the formulation up to 100%, and suitably the total amount of solvent may be present in the range of from about 20 to about 95% by weight of the non-aqueous composition.

Suitably the solvent comprises glycerin present from about 35 to about 75%. In one embodiment the glycerin is present from about 50 to about 70% by weight of the non-aqueous composition.

Suitably the solvent comprises polyethylene glycol present from about 0.1% to about 40% by weight of the non aqueous composition. In one embodiment the polyethylene glycol is present from about 15 to about 25% by weight of the non-aqueous composition.

In order to produce a composition that is smooth and does not show any signs of stickiness, use of a particular ratio of carboxyvinyl polymer to polyethylene glycol is desirable.

Advantageously, the ratio of carboxyvinyl polymer to polyethylene glycol is in the range of about 1:15 to about 1:30.

A dentally acceptable abrasive may optionally be added to the non-aqueous composition. Advantageously, the presence or absence of a dentally acceptable abrasive as well as the amount of such abrasive may be used to selectively control the abrasivity of the dentifrice composition made with the non-aqueous compositions of the invention. By way of example, and if present, the bioactive glass may provide an acceptable amount of abrasivity for the non-aqueous composition depending upon the ultimate use. By further way of example, a desired amount of dentally acceptable abrasive may be added to increase the abrasivity of the overall non-aqueous composition.

Suitable abrasives for use in the non-aqueous composition include, for example, amorphous, gelled, precipitated or fumed silica, zinc orthophosphate, sodium bicarbonate (baking soda), plastic particles, alumina, hydrated alumina, calcium carbonate, calcium pyrophosphate, insoluble metaphosphates or mixtures thereof.

The silica abrasive may be a natural amorphous silica, for instance diatomaceous earth; or a synthetic amorphous silica such as a precipitated silica. By way of example, silica abrasives include those marketed under the following trade names Zeodent, Sident, Sorbosil or Tixosil by Huber, Degussa, Ineos and Rhodia respectively.

Suitably a silica abrasive is present in an amount up to 25% by weight of the total composition, for example from 2 to 20% by weight for example from 5 to 15% by weight of the total composition.

Generally, an amount of abrasive suitable for use in the non-aqueous composition of the present invention will be empirically determined to provide an acceptable level of cleaning and polishing, in accordance with the techniques well known in the art. Suitably, the abrasive is present in an amount from about 0 to about 60%, typically from about 5 to about 30%, by weight of the non-aqueous composition.

The non-aqueous compositions of the invention may additionally optionally contain one or more oral care active agents conventionally used in dentifrice formulations. Such agents may include, by way of example, a fluoride source, a desensitizing agent, an anti-calculus agent, an anti-erosion agent, an antimicrobial agent, an anti-plaque agent, a whitening agent, an oral malodour agent or a mixture of at least two thereof.

Suitable sources of fluoride ions for use in the compositions of the present invention include an alkali metal fluoride such as sodium fluoride, an alkali metal monofluorophosphate such a sodium monofluorophosphate, stannous fluoride, or an amine fluoride in an amount to provide from 25 to 3500 pm of fluoride ions, preferably from 100 to 1500 ppm.

In addition to or as an alternative to the bioactive glass, a further desensitizing agent, including a tubule blocking agent or a nerve desensitizing agent and mixtures thereof, for example as described in WO 02/15809 (Block) may be included in a composition according to the invention. Such further optional desensitizing agent(s) include a strontium salt such as strontium chloride, strontium acetate or strontium nitrate or a potassium salt such as potassium citrate, potassium chloride, potassium bicarbonate, potassium gluconate and especially potassium nitrate.

Polyphosphates are known to help retard calculus formation and are examples of anticalculus agents suitable for use in the invention. A polyphosphate is generally understood to consist of two or more phosphate groups arranged primarily in a linear configuration, although some cyclic derivatives may be present. Polyphosphates of use in the invention include pyrophosphates, polyphosphates having three or more polyphosphate groups such as sodium tripolyphosphate, and polyphosphates having four or more polyphosphate groups such as tetrapolyphosphate and hexametaphosphate among others.

Compositions of the invention may further comprise an antierosion agent, for example a polymeric mineral surface active agent as described in WO 04/054529 (Procter & Gamble).

Compositions of the present invention will contain additional formulating agents such as flavouring agents, sweetening agents, opacifying or colouring agents and preservatives, selected from those conventionally used in an oral hygiene composition art for such purposes.

In general, the optional agents may be used in a minor amount or proportion of the overall formulation. By way of example, such components are usually present in from about 0.001 to about 5% by weight of the non-aqueous composition.

The dentifrice composition typically has a viscosity suitable for application to the oral cavity. The viscosity will vary depending on the type of dentifrice composition made and the ultimate use thereof. One of skill in the art can readily prepare compositions with suitable viscosities for use in the oral cavity from the teachings provided herein.

The compositions according to the present invention may be prepared by admixing the ingredients in the appropriate relative amounts in any order that is convenient.

The invention is further illustrated by the following Examples.

Example 1—Non-Aqueous Composition (Betaine with Taurate)

| Ingredient | Function | % w/w |
| --- | --- | --- |
| Glycerol | Formulation Solvent | 58.39 |
| Polyethylene Glycol 400 | Formulation Solvent | 20.00 |
| Silicon Dioxide | Thickener | 10.00 |
| NovaMin | Desensitising Agent | 5.00 |
| Cocamidopropyl Betaine | Foaming Agent | 1.20 |
| Sodium Methyl Cocoyl Taurate | Foaming Agent | 1.20 |
| Sodium Monofluorophosphate | Oral Heath Active Agent | 1.08 |
| Titanium Dioxide | Opacifier | 1.00 |
| Carbomer Homopolymer | Thickener | 0.75 |
| Sodium Saccharin | Sweetener | 0.35 |
| Flavour | Flavour | 1.03 |

Example 2—Non-Aqueous Composition (Betaine with Alkyl Sulphate)

| Ingredient | Function | % w/w |
| --- | --- | --- |
| Glycerol | Formulation Solvent | 59.33 |
| Polyethylene Glycol 400 | Formulation Solvent | 20.00 |
| Silicon Dioxide | Thickener | 10.00 |
| NovaMin | Desensitising Agent | 5.00 |
| Cocamidopropyl Betaine | Foaming Agent | 0.36 |
| Sodium Lauryl Sulphate | Foaming Agent | 1.10 |
| Sodium Monofluorophosphate | Oral Heath Active Agent | 1.08 |
| Titanium Dioxide | Opacifier | 1.00 |
| Carbomer Homopolymer | Thickener | 0.75 |
| Sodium Saccharin | Sweetener | 0.35 |
| Flavour | Flavour | 1.03 |

Example 3—Sensory Evaluation of Non-Aqueous Compositions of the Invention

Study Objectives

The objectives of these studies were to evaluate the texture profile of several detergent systems.

1. Study 1—Attribute Diagnostic Tests

The dentifrice compositions evaluated included control formulations 1-3 (containing SLS as the sole surfactant component) and dentifrice compositions according to the invention, D1-D2.

| Ingredient | Control 1 | Control 2 | Control 3 | D1 | D2 |
| --- | --- | --- | --- | --- | --- |
| Glycerol | 62.77 | 62.57 | 62.37 | 62.41 | 61.47 |
| Sodium Lauryl Sulphate | 1.10 | 1.30 | 1.50 | 1.10 | — |
| Cocoamidopropyl Betaine | — | — | — | 0.36 | 1.20 |
| Sodium Methyl Cocoyl Taurate | — | — | — | — | 1.20 |
| Polyethylene Glycol 400 | 20.00 | 20.00 | 20.00 | 20.00 | 20.00 |
| Silicon Dioxide | 8.00 | 8.00 | 8.00 | 8.00 | 8.00 |
| NovaMin | 5.00 | 5.00 | 5.00 | 5.00 | 5.00 |
| Titanium Dioxide | 1.00 | 1.00 | 1.00 | 1.00 | 1.00 |
| Carbomer Homopolymer | 0.75 | 0.75 | 0.75 | 0.75 | 0.75 |
| Sodium Saccharin | 0.35 | 0.35 | 0.35 | 0.35 | 0.35 |
| Flavour | 1.03 | 1.03 | 1.03 | 1.03 | 1.03 |

The sensory attributes evaluated were: texture attribute (foam intensity, foam consistency, foam dispersion, foam density); clean teeth sensation and overall liking of the mouthfeel. Seven panelists from the project team were recruited. Samples were blinded, labelled with a three-digit number and presented randomly to the panelists. No statistical analysis was applied due to the low number of panelists.

The samples were perceived as follows:

| | Foam systems (concentration % w/w) | | | | |
| --- | --- | --- | --- | --- | --- |
| | Control 1 1.1% SLS | Control 2 1.3.% SLS | Control 3 1.5% SLS | D1 1.1% SLS - 0.36% TB | D2 1.2% AD- 1.2% TB |
| Mouthfeel liking | 5.5 like slightly | 5.2 like slightly | 4.8 like slightly | 5.6 like moderately | 5.0 like slightly |
| Dispersion of the foam | 3.8 very easy | 3.7 very easy | 3.5 moderately easy | 3.8 very easy | 3.7 very easy |

-continued

| | Foam systems (concentration % w/w) | | | | |
|---|---|---|---|---|---|
| | Control 1 1.1% SLS | Control 2 1.3.% SLS | Control 3 1.5% SLS | D1 1.1% SLS - 0.36% TB | D2 1.2% AD- 1.2% TB |
| Consistency of the foam | 2.5 too thin | 2.3 too thin | 2.6 Just about right | 2.8 Just about right | 2.6 Just about right |
| Foam intensity | 2.9 moderately foaming | 2.8 moderately foaming | 3.4 very foaming | 3.6 very foaming | 4.6 extremely foaming |
| Foam density | 2.4 slightly dense | 2.7 moderately dense | 2.7 moderately dense | 3.0 moderately dense | 2.7 moderately dense |
| Clean teeth sensation | 4.1 very clean | 4.0 very clean | 4.0 very clean | 4.0 very clean | 4.4 very clean |

2. Study 2—Descriptive Profile of the AD/TB and SLS/TB

The objectives of the study were to obtain a complete comparison of the taste and mouthfeel profile of toothpaste formulations (D1 and D2 referred to above) versus a control formulation—Control 4 (1.1% w/w SLS).

The formulation details of the Control 4 composition were as follows:

| | |
|---|---|
| Glycerin | 56.74 |
| PEG 400 | 20.00 |
| Silica | 13.00 |
| Calcium Sodium phosphosilicate | 5.00 |
| Sodium Lauryl Sulphate | 1.10 |
| Sodium Monofluorophosphate | 1.08 |
| Aroma # | 1.03 |
| Titanium Dioxide | 1.00 |
| Carbomer | 0.70 |
| Potassium Acesulfame | 0.35 |

Samples were blinded, labelled with a three-digit number and presented randomly to fifteen professional panelists.

The sensory attributes evaluated were texture attributes (foam intensity, foam density, foam dispersion, smoothness) and taste attributes (sweetness intensity, bitterness intensity; flavour intensity) and clean teeth sensation. The organoleptic profiles of the samples were perceived as follows:

| Sensory attributes | Control 4 1.1% w/w SLS | D1 1.1% w/w SLS - 0.36% w/w TB | p-value | D2 1.2% w/w AD - 1.2% w/w TB | p-value |
|---|---|---|---|---|---|
| Foam intensity | 34.8 | 43.3 | $p < 0.001$ | 49.1 | $p < 0.001$ |
| Foam density | 20.6 | 20.8 | Ns | 27.6 | $p < 0.001$ |
| Dispersion of the paste | 45.6 | 42.7 | Ns | 49.5 | $p < 0.001$ |
| Smoothness of the paste | 41.4 | 40.0 | Ns | 39.5 | Ns |
| Flavour intensity | 52.1 | 59.1 | $p < 0.001$ | 57.0 | $p < 0.001$ |
| Bitterness | 30.7 | 28.1 | $p = 0.05$ | 26.1 | $p < 0.001$ |
| Sweetness | 24.3 | 26.0 | $p < 0.05$ | 22.4 | Control is sweeter at $p < 0.05$ |
| Clean sensation | 59.3 | 65.0 | $p < 0.005$ | 61.3 | $p = 0.06$ |

Conclusion:

Tego Betain/Adinol and Tego Betain/SLS detergent systems improved the foam characteristics of the compositions relative to the SLS system alone, without modifying significantly taste characteristics. The Tego Betain/Adinol composition provided the best performance in terms of foam.

Study 3—Descriptive Profiles of Single Formulations and Mixed Combinations of Tego Betain (TB) and Adinol (AD)

The objectives of the study were to identify and quantify differences in textural elements between formulations comprising SLS, Tego Betain or Adinol as the sole surfactant, and formulations comprising a combination of surfactants i.e. Tego Betain/Adinol and Tego Betain/SLS.

The composition of the toothpastes tested was as follows.

| Material | TB/AD % w/w | TB/SLS % w/w | TB % w/w | SLS % w/w | AD % w/w |
|---|---|---|---|---|---|
| Glycerin | 59.47 | 60.27 | 60.67 | 60.67 | 60.67 |
| Polyethylene Glycol 400 | 20.00 | 20.00 | 20.00 | 20.00 | 20.00 |
| Silicon Dioxide | 10.00 | 10.00 | 10.00 | 10.00 | 10.00 |
| NovaMin | 5.00 | 5.00 | 5.00 | 5.00 | 5.00 |
| Cocoamidopropyl Betaine (Tego Betain) | 1.20 | 0.40 | 1.20 | N/A | N/A |
| Sodium Methyl Cocoyl Taurate (Adinol) | 1.20 | N/A | N/A | N/A | 1.20 |
| Sodium Lauryl Sulfate | N/A | 1.20 | N/A | 1.20 | N/A |
| Titanium Dioxide | 1.00 | 1.00 | 1.00 | 1.00 | 1.00 |
| Carbomer | 0.75 | 0.75 | 0.75 | 0.75 | 0.75 |
| Sodium Saccharin | 0.35 | 0.35 | 0.35 | 0.35 | 0.35 |

-continued

| Material | TB/AD % w/w | TB/SLS % w/w | TB % w/w | SLS % w/w | AD % w/w |
|---|---|---|---|---|---|
| Flavour | 1.03 | 1.03 | 1.03 | 1.03 | 1.03 |
| Total | 100.00 | 100.00 | 100.00 | 100.00 | 100.00 |

Samples were blinded, labelled with a three-digit number and presented randomly to fifteen professional panelists.

Five sensory attributes describing the mouthfeel characteristics of the toothpastes were evaluated. The attributes were: foam intensity, foam density, foam consistency, foam dispersion and lathering of the foam. ANOVA with $\alpha=5\%$ was applied and LSD were calculated to establish any significant difference between the samples and control.

The organoleptic profiles of the samples were perceived as follows:

| | | | | Mixed Combinations | |
|---|---|---|---|---|---|
| | | Single formulations | | 0.4% | 1.2% |
| Sensory attributes | 1.2% w/w SLS | 1.2% w/w TB | 1.2% w/w AD | w/w TB + 1.2% w/w SLS | w/w TB + 1.2% w/w AD |
| Foam Intensity | 46.87 | 48.52 ns | 48.44 ns | 63.19* | 65.33* |
| Foam Density | 34.69 | 30.96 ns | 33.17 ns | 44.00* | 43.88* |
| Foam consistency | 18.86 | 23.13 ns | 26.68* | 33.04* | 37.95* |
| Lathering effect | 63.20 | 65.47 ns | 66.00 ns | 75.87* | 75.91* |
| Dispersion of the paste | 34.12 | 34.97 ns | 33.47 ns | 35.78 ns | 36.74 ns | ns = no significant difference between the toothpaste formulations and the SLS formulation
*= significant difference (p < 0.001) between the toothpaste formulations and the SLS formulation The formulation with 1.2% w/w Tego Betain was not significantly different from the formulation with 1.2% w/w SLS in terms of foam intensity, foam density, foam consistency and lathering of foam.

The formulation with 1.2% w/w Adinol was not significantly different from the formulation with 1.2% w/w SLS in terms of foam intensity, foam density and lathering of foam, but had a foam consistency significantly (p<0.001) thicker.

The foam characteristics (intensity, density, consistency and lathering) of a 1.2% w/w SLS formulation with 0.4% w/w of Tego Betain was significantly (p<0.001) better than those of a formulation with 1.2% w/w SLS only.

The foam characteristics (intensity, density, consistency and lathering effect) of a 1.2% w/w Tego Betain formulation with 1.2% w/w Adinol was significantly (p<0.001) better than those of a formulation with 1.2% w/w SLS only.

There was no significant difference between the single formulations and the mixed combinations and the 1.2% w/w SLS control with regards to the dispersion of the foam during brushing.

Overall the mixed combinations were significantly (p<0.001) foamier than the single formulations. The foam of these dual detergent systems was thicker with small bubbles and the foam appeared soon after the start of the brushing. There was no difference in terms of foam characteristics within the single formulations or the mixed combinations.

Conclusions:

In terms of foam characteristics, there was parity between toothpaste formulations with 1.2% w/w SLS or 1.2% w/w Tego Betain. A 1.2% w/w Adinol formulation also had the same foaming characteristics (intensity, density and lathering) except the foam consistency was thicker.

The addition of Tego Betain (0.4% w/w) to a 1.2% w/w SLS formulation significantly (p<0.001) improved the foam characteristics of the toothpaste. The paste was foamier and the foam had a better quality (thicker with smaller bubbles) and the toothpaste foamed at the start of the brushing (lathering).

Toothpaste formulations with an Adinol/Tego Betain blend were significantly foamier than formulations with SLS only. The foam was thicker with smaller bubbles and the toothpaste foamed soon after the start of the brushing.

The degree to which the foam spread all around the mouth (dispersion of the foam) was not influenced by the composition of the detergent system.

What is claimed is:

1. A non-aqueous dentifrice composition comprising a non-aqueous carrier wherein the carrier comprises glycerin in an amount from 50% to 70% by weight of the composition; polyethylene glycol in an amount from 15 to 25% by weight of the composition; a thickening agent consisting of from 0.3% to 1.0% by weight of the composition of a carboxyvinyl polymer and from 5.0 to 15.0% by weight of the composition of a thickening colloidal hydrated silica; and a surfactant system consisting of a first surfactant which is a betaine in an amount from 0.05% to 4% by weight of the composition and a second surfactant which is a $C_{10\text{-}20}$ alkyl sulphate in an amount from 0.5 to 1.5% by weight of the composition.

2. A composition according to claim 1 wherein the betaine is cocoamidopropyl betaine.

3. A composition according to claim 1 wherein the $C_{10\text{-}20}$ alkyl sulphate is sodium lauryl sulphate.

4. A composition according to claim 1 comprising an oral care active agent selected from a fluoride source, a desensitizing agent, an anti-calculus agent, an anti-erosion agent, an antimicrobial agent, an anti-plaque agent, a whitening agent, an oral malodour agent or a mixture of at least two thereof.

5. A composition according to claim 1 wherein the betaine is present in an amount from 0.2 to about 2% by weight of the composition.

* * * * *